(12) United States Patent
Abboud et al.

(10) Patent No.: US 6,761,714 B2
(45) Date of Patent: *Jul. 13, 2004

(54) LEAK DETECTION SYSTEM

(75) Inventors: Marwan Abboud, Pierrefonds (CA);
Johnny Al Asmar, Montréal (CA);
John W. Lehmann, Wayland, MA (US)

(73) Assignee: CryoCath Technologies Inc., Kirkland (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/124,560

(22) Filed: Apr. 17, 2002

(65) Prior Publication Data

US 2002/0115989 A1 Aug. 22, 2002

Related U.S. Application Data

(62) Division of application No. 09/489,707, filed on Jan. 24, 2000, now Pat. No. 6,569,158.
(60) Provisional application No. 60/117,175, filed on Jan. 25, 1999.

(51) Int. Cl.$^7$ .............................................. A61B 18/18
(52) U.S. Cl. ............................. 606/20; 606/21; 606/23; 607/96
(58) Field of Search .............................. 606/20–26, 32, 606/34, 40–52; 607/98, 100, 101, 105, 113

(56) References Cited

U.S. PATENT DOCUMENTS

| | | | |
|---|---|---|---|
| 3,859,986 A | 1/1975 | Okada et al. ................. 128/7 |
| 4,072,152 A | 2/1978 | Linehan ................... 128/303.1 |
| 4,206,609 A | 6/1980 | Durenec .......................... 62/6 |
| 4,522,194 A | 6/1985 | Normann ................... 128/1 D |
| 4,998,933 A | 3/1991 | Eggers et al. ................. 606/41 |
| 5,139,496 A | 8/1992 | Hed ............................ 606/23 |
| 5,275,595 A | 1/1994 | Dobak, III ................... 606/23 |
| 5,344,398 A | 9/1994 | Hara ............................ 604/96 |
| 5,758,505 A | 6/1998 | Dobak, III et al. .............. 62/6 |
| 5,779,731 A | * 7/1998 | Leavitt ....................... 606/194 |
| 5,807,391 A | 9/1998 | Wijkamp |
| 5,860,970 A | 1/1999 | Goddard et al. .............. 606/23 |
| 6,057,689 A | * 5/2000 | Saadat ........................ 324/557 |
| 6,102,046 A | * 8/2000 | Weinstein et al. .......... 128/898 |
| 6,182,666 B1 | 2/2001 | Dobak, III |
| 6,569,158 B1 | * 5/2003 | Abboud et al. ............... 606/20 |

FOREIGN PATENT DOCUMENTS

| | | | |
|---|---|---|---|
| FR | 2766083 | 7/1997 | ............ A61B/1/12 |
| WO | WO99/56639 | 11/1999 | ............ A61B/17/36 |

* cited by examiner

*Primary Examiner*—Rosiland K. Rollins
(74) *Attorney, Agent, or Firm*—Christopher & Weisberg, P.A.

(57) ABSTRACT

A surgical device includes a device body defining a sealed fluid path having a first end and a second end, a refrigerant supply in communication with the first end of the sealed fluid path; and a vacuum source in communication with the second end of the sealed fluid path. Leak detection apparatus can be provided in communication with the sealed fluid path.

15 Claims, 1 Drawing Sheet

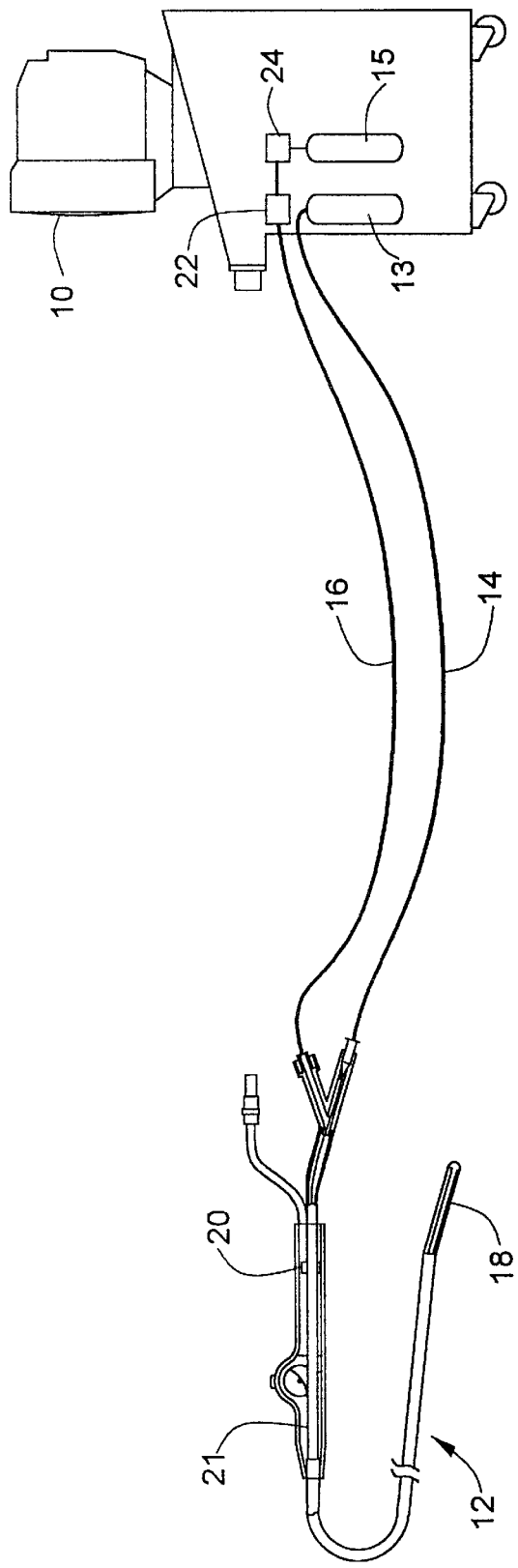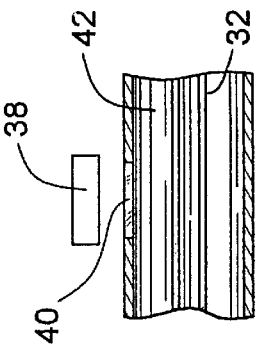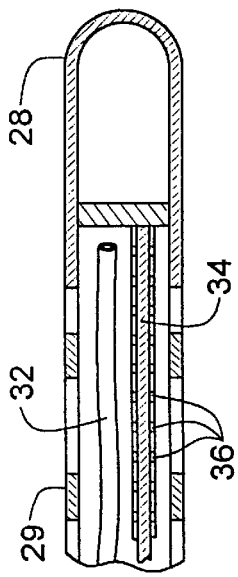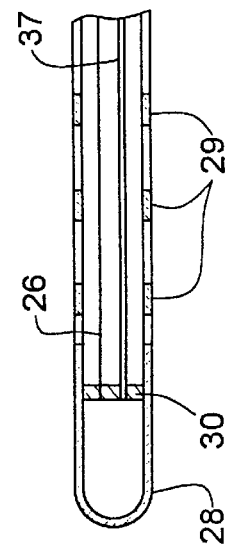

LEAK DETECTION SYSTEM

This application is a divisional of U.S. patent application Ser. No. 09/489,707, filed Jan. 24, 2000 U.S. Pat. No. 6,569,158, which claims priority from U.S. Provisional Patent Application Serial No. 60/117,175, filed Jan. 25, 1999.

STATEMENT REGARDING FEDERALLY SPONSORED RESEARCH

Not applicable.

FIELD OF THE INVENTION

The invention relates to medical devices, and more particularly to minimally invasive surgical systems.

BACKGROUND OF THE INVENTION

Medical devices configured for minimally invasive surgery are rapidly becoming the tools of choice for many surgical procedures. Not only do these devices provide an alternative-to more invasive surgical tools and procedures, but they have also fostered the development of entirely new procedures.

Devices including highly flexible catheters, as well as rigid and semi-flexible probes have received increased attention in recent years and continue to be refined for cardiovascular, pulmonary, urogenital, and other applications. Devices for each of these applications present different technology and material challenges. Angioplasty catheters, for example, can require fluid-tight passages or channels for circulating a cooling fluid (liquid or gas) through a catheter to cool an electro-surgical structure, such as radio frequency ablation electrode, to prevent overheating of the electrode or of surrounding tissue. Similarly, a cooling or cryogenic fluid can be reduce the temperature of a structure, such as an ablation surface, to a therapeutic temperature. Some cooling fluids, however, can be harmful or fatal to the patient if they unintentionally escape from the surgical device.

Although careful fabrication techniques, quality materials, and thorough testing can reduce the chances of cooling fluid leakage, it would be desirable to provide additional system features that further minimize the occurrence of leaks; and should a leak occur, provide features that detect cooling fluid loss or escape immediately so that use of the surgical device can be terminated and patient remediation efforts can be undertaken if required.

SUMMARY OF THE INVENTION

The present invention provides an improved surgical device including a device body defining a sealed fluid path having a first end and a second end, a refrigerant supply in communication with the first end of the sealed fluid path, and a vacuum source in communication with the second end of the sealed fluid path. Leak detection apparatus can be provided in communication with the sealed fluid path.

Exemplary leak detection apparatus include an impedance measurement circuit, an infrared sensor, and a pulsed ultrasonic device. A control unit that is in communication with the leak detection apparatus is responsive to output from the leak detection apparatus to control fluid flow through the sealed fluid flow path.

BRIEF DESCRIPTION OF THE DRAWINGS

The invention will be more fully understood from the following detailed description taken in conjunction with the accompanying drawings in which:

FIG. 1 is a schematic view of a minimally invasive surgical system including a leak detection system in accordance with the invention;

FIG. 2 illustrates an exemplary cryocatheter tip with a leak detection circuit;

FIG. 3 illustrates a porous, insulated, conductive wire within a cryocatheter tip; and FIG. 4 illustrates another leak detection device.

DETAILED DESCRIPTION OF THE INVENTION

In the discussion which follows, "surgical device" is intended to encompass any surgical implement used in association with human or animal medical treatment, diagnosis, study, or analysis. More particularly, a surgical device is intended to encompass any implement or portion thereof that is entirely or partially inserted into a human or animal body by any means of entry, such as through a natural body orifice, an incision, or a puncture. The term surgical device is not intended to connote a limitation to treatment of a single body system, organ, or site. The surgical device can be rigid as a thick steel pipe, completely flexible and pliant like a thread, or have a flexibility between the two extremes. The surgical device can have a diameter that ranges from inches to microns.

As used herein, "fluid" is intended to encompass materials in a liquid state, a gas state, or in a transition state between liquid and gas, and liquid and solid. The fluid can be a "cryogenic fluid" capable of reaching or creating extremely cold temperatures well below the freezing point of water, such as below minus 20 degrees Centigrade; a "cooling fluid" that does not reach or create temperatures below the freezing point of water; a fluid capable of transferring heat away from a relatively warmer structure or body tissue; a fluid capable of transferring heat to a relatively cooler structure or body tissue; a fluid at or capable of creating a temperature between the freezing and boiling points of water; and a fluid at or capable of reaching or creating a temperature above the boiling point of water.

A "fluid path" as used herein is intended to encompass any boundary, channel or guide through which a fluid can travel. It can include concentrically disposed catheters, multi-lumen catheters, or a single loop of tubing within a sheath. The fluid path can also include connectors and valves, as well as passages in support equipment, such as the console disclosed herein.

Referring now to FIG. 1, an exemplary surgical device is illustrated for minimally invasive surgery. The surgical device includes a console 10 and a multi-lumen catheter 12. The console 10 houses electronics and software for controlling and recording a surgical procedure, such as ablation, and it controls delivery of liquid refrigerant under high pressure from a supply container 13, through an umbilical 14, to the catheter 12. A second umbilical 16 is provided for transferring refrigerant from the catheter 12 to console 10. The console 10 is provided with apparatus 15 for recovery of expanded refrigerant vapor from the catheter and recompression of the vapor.

Either or both of the catheter 12 and the console 10 can be provided with detection devices that are in electrical communication with the console and which provide a signal output that can be representative of an event that indicates flow path integrity loss or a leak within a sealed catheter and/or console. As shown in FIG. 1, a first detection device or leak detector 18 can be provided in a body or tip portion of the catheter 12. A second leak detector 20 can be provided in the handle portion 21 of the catheter 12; and a third leak detector 22 can be provided in the console 10. The console 10 can be configured to respond to signal output from the leak detectors and initiate a predetermined sequence of events, such as discontinuing refrigerant injection, changing the pressure within the system, and controlling removal of refrigerant from the catheter 12.

The purpose and function of the leak detectors is better understood once another feature of the invention is introduced, namely, a vacuum pump 24, as shown in FIG. 1 in fluid communication with a catheter 12. The third leak detector 22 can be interposed between the vacuum pump 24 and the catheter 16. The vacuum pump 24 is controllable to reduce the pressure within the return lumen of the catheter 12 and the second umbilical 16 to provide a pressure ranging from a pure vacuum to a pressure just below a patient's blood pressure. For example, the vacuum can maintain a selected pressure between 80 mm Hg and 0 mm Hg. The provision of reduced pressure within the return flow path of the catheter significantly enhances patient safety because, should a leak occur, refrigerant will not squirt from the leak into the patient. Rather, bodily fluids in the treatment site will be aspirated into the catheter whereupon they are sensed by one or more of the leak detectors. In one mode of operation, when a leak is detected, the refrigerant injection is turned off automatically and vacuum is kept on to ensure that no refrigerant enters the patient's body.

Although a single type of leak detector could be functional, an exemplary embodiment of the invention is provided with three different types of leak detectors for enhanced detection probability. For example, the first leak detector 18 can be a simple circuit formed by a wire, such as a pull-wire used to help steer the catheter tip, and a conductive catheter tip portion. Specifically, as shown in FIG. 2, a wire 26 is electrically isolated from a metal catheter tip 28 and metal electrode rings 29. In the illustrated embodiment, the wire is secured to a non-conductive support element 30. Also shown is a refrigerant injection tube 32. The electrical impedance between the wire 26 and the catheter tip 28 is monitored. If a liquid enters the catheter 12 and touches the wire 26 and the tip 28, a short is created which is detectable by circuitry in the console. Alternatively, the wire 26 and one or more of the electrode rings 29 can be included in the impedance circuit.

However, some catheters 12 may include multiple conductors running within one or more lumens and electrical insulation on the conductors is necessary to avoid unwanted electrical connections and interferences. Many such catheters also contain uninsulated wires, for example as mechanical deflectors to alter catheter configuration, or for example as stiffening agents to alter catheter flexibility or pushability. However, if the pull wire (or other wire that is part of the leak detection circuit) contacts another uninsulated wire, electrode ring or other conductive element, a false leak detection signal could be generated. Accordingly, a form of insulation that provides mechanical insulation while allowing fluid conductivity is desirable.

FIG. 3 discloses a wire 34 (such as a pull wire) that is part of the leak detection circuit. The wire 34 is covered with a porous material 36, such as a fabric, salt-depleted polymer, or laser drilled polymer, that provides mechanical insulation in the dry state by the physical bulk and separation of the porous material, which allows passage of ionic fluids to the thus insulated wire to complete the electrical leak detection circuit.

Although the first leak detector 18 is well suited for detecting leaks at or near the distal end of the catheter 12, a leak may develop between the distal end and the handle portion 21 of the catheter and an infrared sensor can be disposed in the handle as the second leak detector 20. As soon as the first and/or second leak detectors output a signal to the console indicative of a leak, the refrigerant injection can be stopped. In an exemplary embodiment, shown in FIG. 4, an infrared sensor 38 with a wavelength sensitive to blood composition is disposed in sensing range with a transparent window 40 or tube along or forming part of the return fluid flow path 42.

Even though refrigerant injection is stopped, it can still be desirable to apply vacuum to the catheter to withdraw refrigerant already introduced into the catheter, along with refrigerant contaminated blood. Thus, a third leak detector 22 (shown in FIG. 1) is provided further downstream in the fluid flow path to not only provide a last opportunity for detection, but to also detect when a selected volume of blood has been aspirated (a relatively small amount) and to then terminate vacuum operation or aspiration. Depending on placement of the third leak detector, it can prevent blood contamination of the entire fluid flow path within the console 10.

Although the invention has been shown with respect to exemplary embodiments thereof, various other changes, omissions and additions in form and detail thereof may be made therein without departing from the spirit and scope of the invention.

What is claimed is:

1. A surgical device comprising:
   a device body defining a sealed fluid path having a first end and a second end;
   a supply of a cryogenic fluid in communication with the first end of the sealed fluid path;
   a vacuum source in communication with the second end of the sealed fluid path;
   a leak detection apparatus in direct fluid contact with the sealed fluid path, said leak detection apparatus having at least a portion of an impedance measurement circuit in the sealed fluid path, said impedance measurement circuit including a conductive portion of the device body and a wire disposed within the device body, the wire being electrically isolated from the conductive portion of the device body, and
   a fluid porous coating disposed around a portion of the wire.

2. The surgical device of claim 1, wherein the fluid porous coating includes a fabric.

3. The surgical device of claim 1, wherein the fluid porous coating includes a salt-depleted polymer.

4. The surgical device of claim 1, wherein the fluid porous coating includes a laser-drilled polymer.

5. The surgical device of claim 1, further comprising a control unit that is in communication with the leak detection apparatus, wherein the control unit is responsive to output from the leak detection apparatus to control fluid flow through sealed fluid path.

6. The surgical device of claim 1, wherein the device body includes a catheter and the refrigerant cryogenic fluid is capable of reducing the temperature within a portion of the catheter to a temperature below minus 20 degrees Centigrade.

7. A surgical device comprising:

a catheter having proximal and distal end portions, and having a sealed flow lumen, the flow lumen having first and second end portions;

a supply of a cryogenic fluid in communication with the first end portion of the flow lumen;

a vacuum source in communication with the second end portion of the flow lumen;

an impedance measurement circuit disposed inside the flow lumen, including a first conductive element disposed on the distal end portion of the catheter, and a second conductive element disposed within the sealed flow lumen, the first conductive element being electrically isolated from the second conductive element.

8. The surgical device of claim 7, wherein the first conductive element is a metal catheter tip.

9. The surgical device of claim 7, wherein the second conductive element is a metal wire.

10. The surgical device of claim 7, further comprising a fluid-permeable insulation element disposed around the second conductive element.

11. The surgical device of claim 10, wherein the second conductive element is a metal wire.

12. The surgical device of claim 10, wherein the fluid-permeable insulation element is porous to allow passage of ionic fluids.

13. The surgical device of claim 10, wherein the fluid-permeable insulation element is a fabric.

14. The surgical device of claim 10, wherein the fluid-permeable insulation element is a salt-depleted polymer.

15. The surgical device of claim 10, wherein the fluid-permeable insulation element is a laser-drilled polymer.

* * * * *